United States Patent [19]

Boyle

[11] Patent Number: 4,684,657
[45] Date of Patent: Aug. 4, 1987

[54] BENZENESULPHONAMIDE DERIVATIVES
[75] Inventor: John T. A. Boyle, Cookham, England
[73] Assignee: John Wyeth & Brother Limited
[21] Appl. No.: 782,258
[22] Filed: Sep. 30, 1985
[30] Foreign Application Priority Data
  Oct. 3, 1984 [GB] United Kingdom ............... 8424979
[51] Int. Cl.$^4$ ................. A61K 31/495; C07D 401/12
[52] U.S. Cl. ................................. 514/313; 514/248;
  514/253; 544/235; 544/293; 544/363; 544/383;
  544/391; 546/160
[58] Field of Search .................. 544/363, 293, 235;
  514/253, 248, 313; 546/160

[56] References Cited
U.S. PATENT DOCUMENTS

| 3,324,129 | 6/1967 | Baget et al. ........................... 544/363 |
| 3,935,229 | 1/1976 | Giudicelli et al. .................. 544/363 |
| 3,992,382 | 11/1976 | Coverdale et al. ................. 544/363 |
| 4,025,629 | 5/1977 | Coverdale ........................... 544/363 |
| 4,159,331 | 6/1979 | McCall ................................ 544/363 |
| 4,167,567 | 9/1979 | McCall ................................ 544/363 |

FOREIGN PATENT DOCUMENTS 2021567 4/1979 United Kingdom .
2021568 4/1979 United Kingdom .

OTHER PUBLICATIONS

*Federation Proceedings*, 42, 162-66 (1983).

Primary Examiner—Glennon H. Hollrah
Assistant Examiner—James H. Turnipseed
Attorney, Agent, or Firm—George Tarnowski

[57] ABSTRACT

Compounds having the formula

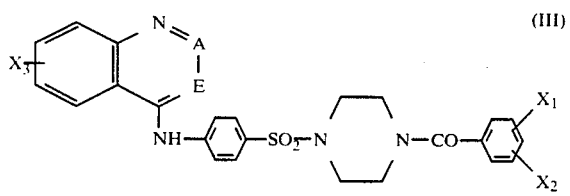

wherein $X_1$ and $X_2$ are independently hydrogen, halogen, trifluoromethyl, lower alkyl or lower alkoxy; $X_3$ is halogen or trifluoromethyl; one of A and E is CH and the other is CH or N and their pharmaceutically acceptable acid addition salts are useful as pharmaceuticals, in particular as anti-hypertensive agents. Novel 1-[4-(amino or nitro)benzenesulphonyl]-4-benzoylpiperazines are also disclosed as intermediate compounds.

8 Claims, No Drawings

BENZENESULPHONAMIDE DERIVATIVES

The invention relates to novel benzenesulphonamide derivatives that are useful as pharmaceuticals, particularly as anti-hypertensive agents. The invention also provides processes for their preparation, pharmaceutical compositions containing them, novel compounds useful as intermediates for the preparation of the said derivatives and a process for the preparation of the intermediate compounds.

The invention provides, as novel benzenesuphonamide derivatives, compounds having the formula (I)

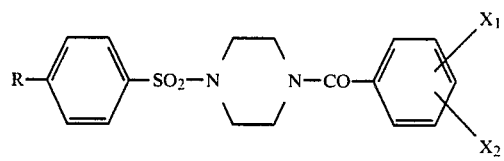
(I)

[wherein $X_1$ and $X_2$ are independently selected from hydrogen, halogen, trifluoromethyl, lower alkyl and lower alkoxy and R is selected from (a) a group having the formula II

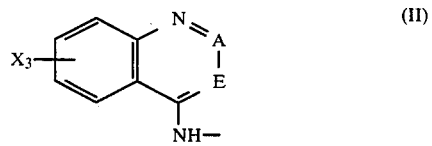
(II)

(where $X_3$ is halogen or trifluoromethyl; one of A and E is CH and the other one of A and E is selected from CH and N) (b) amino and (c) nitro] and the pharmaceutically acceptable acid addition salts of compounds of formula I where R is a group of formula II and acid addition salts of compounds of formula I where R is amino.

The end compounds of the invention are those having formula III

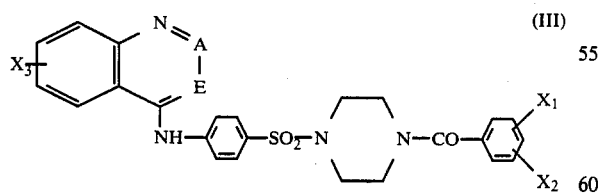
(III)

(where $X_1$, $X_2$, $X_3$, A and E are as defined above) and the pharmaceutically acceptable acid addition salts thereof. These compounds are particularly indicated for use as pharmaceuticals, particularly as anti-hypertensive agents.

When both of A and E are CH, the end compounds of the invention are quinoline derivatives. When A is CH whilst E is N the end compounds of the invention are quinazoline derivatives. Where A is N whilst E is CH the end compounds of the invention are cinnoline derivatives. Advantageously both A and E are CH.

$X_3$ may substitute any of the 5,6,7 and 8 positions of the quinoline, quinazoline or cinnoline ring system, but is preferably at the 7- or 8-position, advantageously the 7-position. Where $X_3$ is at the 7-position, formula III may be represented as IIIa

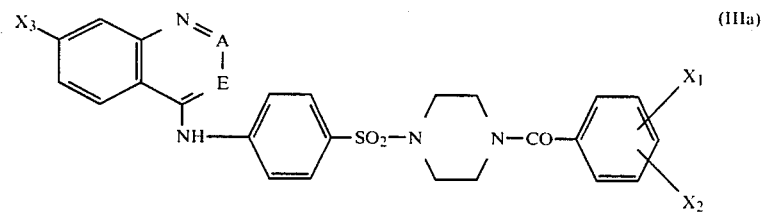
(IIIa)

$X_3$ represents halogen, for instance chlorine or bromine, or trifluoromethyl. $X_3$ is preferably trifluoromethyl. $X_1$ and $X_2$ independently represent hydrogen, halogen (for instance fluorine, chlorine or bromine), trifluoromethyl, lower alkyl (for instance methyl, ethyl, propyl, butyl) or lower alkoxy (for instance methoxy, ethoxy, propoxy, butoxy). The group having the formula

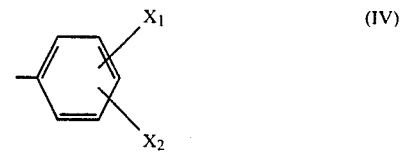
(IV)

is preferably mono (halo or trifluoromethyl)phenyl, advantageously p-fluorophenyl.

The term "lower" as used herein to refer to such groups as alkyl and alkoxy indicates that the group contains up to 6, preferably up to 4, carbon atoms. The group may be in the form of a straight chain or may be branched.

The compounds having formula I where R has formula II or is amino form acid addition salts with acids. Examples of acid addition salts are those formed from inorganic and organic acids and in particular include the sulphate, hydrochloride, hydrobromide, hydroiodide, nitrate, phosphate, sulphonates (for instance the methanesulphonate or p-toluenesulphonate), acetate, maleate, fumarate, tartrate, malonate, citrate and formate.

The end compounds of the invention can be prepared by a process which comprises (a) sulphonylating a compound having the formula (V)

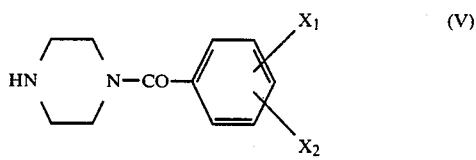
(V)

(where $X_1$ and $X_2$ are as defined above) to introduce the sulphonyl group having formula VI

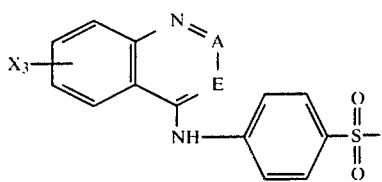

(where $X_3$, A and E are as defined above); or (b) a compound having the formula VII

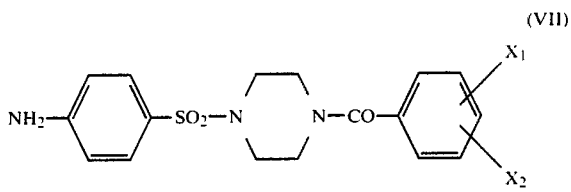

(where $X_1$ and $X_2$ are as defined above) or a salt thereof is reacted with a compound having the formula VIII

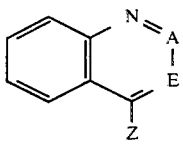

(where $X_3$, A and E are as defined above and Z is a leaving group or atom, preferably a halogen atom such as iodine, bromine or chlorine) and, if desired a compound having formula III is converted into a pharmaceutically acceptable acid addition salt of a compound having formula III or an acid addition salt of a compound having formula III is converted into a compound having formula III.

For the purpose of step (a), the sulphonyl chloride is preferably used as sulphonylating agent. The reaction can be carried out in known manner for sulphonylation of amines. The sulphonylation can be carried out in a suitable solvent, for instance, chloroform or methylene chloride, in the presence of a base to neutralise the hydrogen chloride formed. The base may be provided by using, for instance, an alkali metal carbonate or bicarbonate or a tertiary amine, for instance, triethylamine or an excess of the basic compound having formula V.

The sulphonyl chloride can be prepared from the corresponding sulphonic acid of formula IX

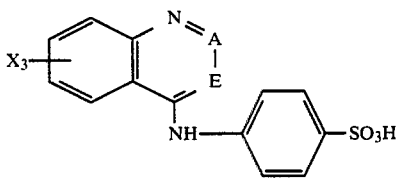

(where $X_3$, A and E are as defined above) in known manner, for example, by the use of thionyl chloride and dimethylformamide. The sulphonic acids having formula IX are known per se in many cases and may be prepared in known manner in other cases, particularly by reacting 4-aminobenzenesulphonic acid with a compound having formula VIII. The preparation of the compounds having formula V is described below.

The reaction of the compound having formula VII with the compound having formula VIII according to step (b) of the process can be carried out in aqueous alcohol with or without acid catalysts. The compounds having formula VIII are generally known or, if new, can be prepared in known manner. The p-aminobenzenesulphonamides having formula VII are novel intermediates provided by this invention and can be prepared as described below.

Once a compound having formula III has been formed, it may be converted into a pharmaceutically acceptable acid addition salt by addition of a suitable acid. If an acid addition salt of a compound having formula III is prepared, the salt may be neutralised with a base to form the compound having formula III.

The novel chemical intermediate compounds provided by this invention are the 4-aminobenzenesulphonamides having formula VII (as shown above), their acid addition salt, and 4-nitrobenzenesulphonamide derivatives having the formula X (as shown below).

The invention also provides a process for the preparation of a 4-aminobenzenesulphonamide derivative having formula VII

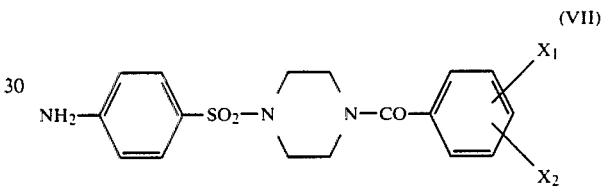

(where $X_1$ and $X_2$ are as defined above) or a salt thereof, wherein a 4-nitrobenzenesulphonamide derivative having the formula X

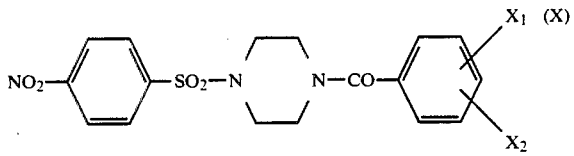

(where $X_1$ and $X_2$ are as defined above) is reduced and, if desired, a compound having formula VII is converted into an acid addition salt thereof or an acid addition salt of a compound having the formula VII is converted into the compound having formula VII.

The reduction of the nitro compound (X) is preferably carried out by means of catalytic reduction.

The invention also provides a process for the preparation of a 4-nitrobenzenesulphonamide derivative having formula X (in which $X_1$ and $X_2$ are as defined above), wherein a compound having the formula V

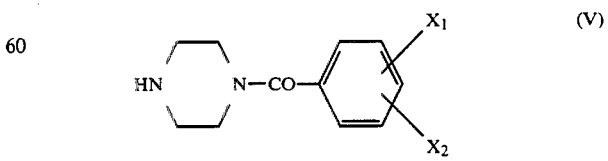

(in which $X_1$ and $X_2$ are as defined above) or a salt thereof is sulphonylated to introduce the 4-nitrobenzenesulphonyl group. As sulphonylating agent 4- nitrobenzenesulphonyl chloride is preferably used. The sulphonylation can be carried out in a suitable solvent, for instance, chloroform or methylene chloride, in the presence of a base to neutralise the hydrogen chloride formed. The base may be provided by using, for instance, an alkali metal carbonate or bicarbonate or a tertiary amine, for instance, triethylamine, or an excess of the basic compound having formula V.

The compounds having formula V are known, at least in some cases. They can be prepared by coupling 1-benzylpiperazine with a compound having the formula XI

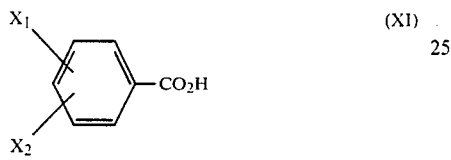

(where $X_1$ and $X_2$ are as defined above) or a reactive derivative thereof to form an amide having the formula XII

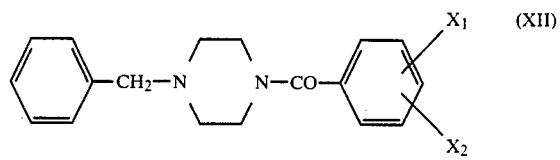

and debenzylating the amide (XII). The amide may be formed by reacting 1-benzylpiperazine with the acid (XI) in the presence of a condensing agent or by reacting 1-benzylpiperazine with a reactive derivative (for instance, acid chloride, acid anhydride or active ester) of the acid (XI). The debenzylation can be carried out by means of catalytic hydrogenation.

The novel compounds having general formula III and their pharmaceutically acceptable salts are indicated for use as anti-hypertensive agents. The compounds may be tested for their response on the blood pressure of spontaneously hypertensive rats in the following procedure:

The blood pressure of male or female conscious rats that are spontaneously hypertensive are measured in a 39° C. constant temperature housing by means of a tail cuff. Rats with systolic pressures below 155 mg Hg are not used. Groups of rats (4 per group) are dosed orally with the test substance in a suitable vehicle or with vehicle alone. Systolic pressures are recorded before dosing and at selected time points afterwards (2 hours, 6 hours and 24 hours).

One of the compounds of the invention is 1-[4-fluorobenzoyl]-4-[4-(7-trifluoromethyl-4-quinolinylamino)benzenesulphonyl]piperazine. A compound related thereto, 1-[(4-fluorophenyl)sulphonyl]-4-[4-(7-trifluoromethyl-4-quinolylamino)benzoyl]piperazine, is known from G.B. 2,021,567A. These two compounds can be represented by the formula (A)

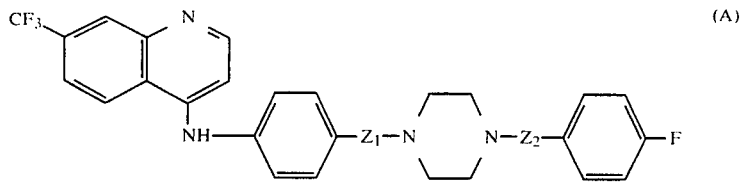

where $Z_1$ is $SO_2$ and $Z_2$ is CO in the case of the invention and $Z_1$ is CO and $Z_2$ is $SO_2$ in the case of the known compound. These two compounds have been tested in the above procedure and the results are presented in the following table.

The compound of the invention was tested as the monoethanolate. The prior art compound was tested as the hydrochloride ⅔ ethanolate.

| Compound of | Dose (millimoles per kg) | Blood pressure (as % of blood pressure before dosing) | | |
|---|---|---|---|---|
| | | After 2 hours | After 6 hours | After 24 hours |
| Prior Art ($Z_1$=CO, $Z_2$=$SO_2$) | 0.03 | 72 | 68 | 71 |
| Invention ($Z_1$=$SO_2$, $Z_2$=CO) | 0.03 | 47 | 38 | 62 |
| | 0.003 | 70 | 54 | 85 |

The results show that the compound of the invention was far more effective than the known compound at the same dose (0.03 millimoles per kg).

The invention also provides a pharmaceutical composition comprising a compound having formula I or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffer, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilised by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient. The invention also includes the compounds in the absence of the carrier where the compounds are in unit dosage form.

The invention is illustrated by the following examples:

EXAMPLE 1

1-[4-Fluorobenzoyl]-4-[4-(7-trifluoromethyl-4-quinolinylamino)benzenesulphonyl]piperazine 4-(7-Trifluoromethyl-4-quinolinylamino)benzenesulphonyl chloride hydrochloride (3.5 g, 0.008 mol) was added portionwise to a cold (10°), well stirred mixture of 1-(4-fluorobenzoyl)piperazine hydrochloride (2.0 g, 0.008 mol) in chloroform (50 ml) and sodium carbonate (10.0 g) in water (50 ml). The cooling bath was removed and the mixture was allowed to warm to room temperature. After half an hour, the mixture was filtered and the filtrate separated. The chloroform layer was dried (MgSO4). The solvent was removed by evaporation to give a yellow gum. The gum was crystallised from ethanol-water, then purified by column chromatography (basic Al2O3-chloroform) followed by recrystallisation from ethanol, to give the pure title compound (0.9 g), m.p. 172°-174.5° C.

Analysis: Found: C, 57.3%; H, 4.63%; N, 9.71%. $C_{27}H_{22}F_4N_4O_3S \cdot C_2H_5OH$ requires C, 57.6%; H, 4.67%; N, 9.30%.

EXAMPLE 2

1-[4-(7-Chloro-4-quinolinylamino)benzenesulphonyl]-4-(4-fluorobenzoyl)piperazine 4-(7-Chloro-4-quinolinylamino)benzenesulphonyl chloride hydrochloride (7.8 g, 0.02 mol) was added portionwise with stirring to a cold mixture of 1-(4-fluorobenzoyl)piperazine hydrochloride (4.9 g, 0.02 mol) in chloroform (250 ml) and sodium carbonate (24.4 g) in water (250 ml). The cooling bath was removed and the mixture was allowed to warm to room temperature. After 1 hour the chloroform layer was separated and dried (MgSO4). The solvent was removed by evaporation to give a brown gum. Crystallisation from ethanol gave the pure title compound (0.53 g), m.p. 235°-237° C.

Analysis: Found: C, 59.5%; H, 4.05%; N, 11.0%. $C_{26}H_{23}ClFN_4O_3S$ requires C, 59.4%; H, 4.41%; N, 10.7%.

EXAMPLE 3

1-[4-Fluorobenzoyl]-4-[4-(7-trifluoromethyl-4-quinolinylamino)benzenesulphonyl]piperazine 1-(4-fluorobenzoyl)-4-(4-nitrobenzenesulphonyl)piperazine is prepared in a similar manner to Examples 1 and 2 by reacting equimolar quantities of 4-nitrobenzenesulphonyl chloride with 1-(4-fluorobenzoyl)piperazine hydrochloride. The reaction product is hydrogenated in ethanol at room temperature at atmospheric pressure with a 5% paladium on charcoal catalyst until hydrogen uptake ceases to yield 1-(4-aminobenzenesulphonyl)-4-(4-fluorobenzoyl)piperazine. Equimolar quantities of this compound and 4-chloro-7-trifluoroquinoline are reacted in 50% aqueous ethanol under reflux to yield the title compound.

I claim:
1. A compound selected from those having the formula

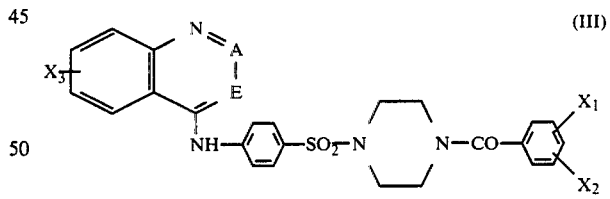

and their pharmaceutically acceptable acid addition salts, wherein $X_1$ and $X_2$ are independently selected from hydrogen, halogen, trifluoromethyl, lower alkyl and lower alkoxy; $X_3$ is selected from halogen and trifluoromethyl; one of A and E is CH and the other one of A and E is selected from Ch and N.

2. A compound as claimed in claim 1, wherein $X_3$ is at the 7-position.

3. A compound as claimed in claim 1, wherein $X_3$ is trifluoromethyl.

4. A compound as claimed in claim 1, wherein both A and E are CH.

5. A compound as claimed in claim 1, wherein one of $X_1$ and $X_2$ is hydrogen and the other one of $X_1$ and $X_2$ is selected from halogen and trifluoromethyl.

6. A compound as claimed in claim 1, wherein the compound having formula III is 1-[4-fluorobenzoyl]-4-[4-(7-trifluoromethyl-4-quinolinylamino)benzenesulphonyl]piperazine and its pharmaceutically acceptable salts.

7. A compound as claimed in claim 1, wherein the compound having formula III is 1-[4-(7-chloro-4-quinolinylamino)benzenesulphonyl]-4-(4-fluorobenzoyl)piperazine.

8. A pharmaceutical composition for anti-hypertensive use comprising an effective quantity of a compound as claimed in claim 1 in association with a pharmaceutically acceptable carrier.

* * * * *